(12) United States Patent
Verona et al.

(10) Patent No.: US 7,323,010 B2
(45) Date of Patent: Jan. 29, 2008

(54) BIOMATERIAL INCLUDING ANIMAL CORNEAL TISSUE

(76) Inventors: Alessandro Verona, Largo Zandonai, 3, 20145 Milano (IT); Roberto Erminio Parravicini, Viale Virginia Reiter, 51/02, 41100 Modena (IT)

( * ) Notice: Subject to any disclaimer, the term of this patent is extended or adjusted under 35 U.S.C. 154(b) by 309 days.

(21) Appl. No.: 10/332,554

(22) PCT Filed: Jul. 10, 2001

(86) PCT No.: PCT/IT01/00363

§ 371 (c)(1),
(2), (4) Date: Jun. 16, 2003

(87) PCT Pub. No.: WO02/04037

PCT Pub. Date: Jan. 17, 2002

(65) Prior Publication Data

US 2004/0044407 A1    Mar. 4, 2004

(30) Foreign Application Priority Data

Jul. 11, 2000   (IT)   .......................... BO2000A0414
Jul. 14, 2000   (IT)   .......................... BO2000A0430

(51) Int. Cl.
*A61L 27/36*    (2006.01)
*A61K 35/60*    (2006.01)

(52) U.S. Cl. ..................... 623/2.14; 623/2.13; 623/5.11
(58) Field of Classification Search ...... 623/2.12–2.19, 623/5.11, 2.42
See application file for complete search history.

(56) References Cited

U.S. PATENT DOCUMENTS 4,793,344 A * 12/1988 Cumming et al. .............. 606/1

FOREIGN PATENT DOCUMENTS

WO    8802263    *   7/1988
WO    8802263        4/1998

OTHER PUBLICATIONS

Document A, Treseler et al., "The relative immunogenicity of corneal epithelium, stroma, and endothelium. The role od major histocompatibility", Transplantation, Feb. 1986.*

* cited by examiner

*Primary Examiner*—Corrine McDermott
*Assistant Examiner*—David A. Izquierdo
(74) *Attorney, Agent, or Firm*—Ladas and Parry LLP

(57) ABSTRACT

Biomaterial including tissues basically obtained from an animal cornea, in particular, from a fish cornea. A cardiac valve (10) which may envisage at least one cusp (15) made with an organic tissue obtained from this particular biomaterial.

20 Claims, 1 Drawing Sheet

BIOMATERIAL INCLUDING ANIMAL CORNEAL TISSUE

TECHNICAL FIELD

The present invention concerns a tissular biomaterial. In particular, such biomaterial can be used for the production of cardiac valves.

The present invention refers to the field of the repair or replacement of human or animal tissues affected by pathological processes, and particularly to the use of a tissular biomaterial derived from the animal cornea made immunologically biocompatible and subjected to processing methods suitable for the attainment of simple or composite products destined for implantation.

BACKGROUND ART

The use is well known, in implantology, of biomaterials of animal or human origin to be inserted in the body of a patient.

Despite the achievement of important targets in the production of prosthetic substitutes derived from the technology of materials and from the treatment of tissues of animal origin, the totality of the characteristics required of a permanent implant have still not been completely fulfilled.

In particular, biological tissues taken from an animal and suitably devitalized are commonly used in the biomedical field as implants or for the production of prostheses. For example, some bovine pericardium or pig's cardiac valvular tissue has been used for the production of cardiac valves.

For instance, the American patent U.S. Pat. No. 4,692,164 describes a cardiac valve whose cusps are made of a biological material explanted from the aorta of an animal or human being.

The American patent U.S. Pat. No. 4,755,593 also describes the use of a treated biomaterial which includes some peritoneal tissue.

Important disadvantages are currently associated with the advantages derived from implants made of animal tissues. To be considered among these is a possible antigenicity, a certain loss of the mechanical characteristics, and the biological degeneration of the tissues.

The efforts of interdisciplinary research are aimed at the search for new biomaterials and the realization of treatment methods of biological tissues capable of improving both the mechanical and biological characteristics.

Nevertheless, the use of this tissue type involves a series of problems since they contain fats and other substances that must be removed by complex treatment before the tissue can be implanted in the living organism.

DISCLOSURE OF INVENTION

The main aim of the present invention is, therefore, that of providing easy to find tissular biomaterial having biological and mechanical characteristics such as to render it compatible, for example, with the making of cardiac valves.

Therefore, according to the present invention, a biomaterial is made to use in medical devices characterized in that it includes tissues basically obtained from an animal cornea, particularly from a fish cornea.

Moreover, an additional aim of the present invention is to produce an innovative cardiac valve utilizing the aforesaid biomaterial.

Therefore, the present invention has the aim of facing up to and solving fundamental aspects relating to the use of a biomaterial as a permanent implant in the human or animal organism. In this context, the biophysical stability of the same plays an important role and the possibility of subsequent processing, such as to make it usable for the construction of simple or composite implants.

Research has been conducted with the aim of identifying a possible source of biological material with the desired potential characteristics. Such research has led to the finding of the material considered most suitable and, within the scope of such, to the identification of a particular component constituting the selected tissue.

In addition, an extraction method from animal cadavers has been prepared of simple and sure realization which does not alter the desired characteristics of the material.

A conservation method of tissue, made inactive, with unchanged mechanical characteristics so as to make it sterile and available for implantation, has also been realized.

The availability of the biological tissue has also been assessed and has proved fully capable of solving the problems correlated with the industrial production of prostheses or implants.

In addition, the removal and processing of the biological tissue under conditions of freshness, i.e. before the development of autolytic phenomena and bacterial degradation, typical of cadaverous tissues, is a characteristic which is fully discharged by the invention.

In more detail, in accordance with the present invention, the tissular biomaterial is produced according to the following stages:

1. Finding and explantation of the organ from which the biomaterial is drawn.
2. Mechanical preparation.
3. Chemical treatment.
4. Construction of the end product (simple or composite).
5. Sterilization and packing.

In particular:

1. Finding and Explantation of the Organ From Which the Biomaterial is Drawn.

Eyeballs of animal cadavers, preferably fish (and within the specific field, tuna fish), free from macroscopic lesions upon detailed objective examination are removed in toto, under optimum conservation conditions (freshness).

The cornea of fish, particularly of tuna, is physiologically able to bear considerable stress, since it can withstand up to 40-50 Atm. of pressure when the fish is underwater.

The eyeballs, for example of a tuna, are removed by skilled personnel and immediately preserved, preferably in phosphate buffer saline solution at pH 7.4 at 4° C. However, alternative preservation solutions can be used.

Organ removal under conditions of freshness and the beginning of the subsequent processing stages in very quick times are of particular importance, in order to prevent enzymatic and/or bacterial degradation phenomena of the biological tissue.

2. Mechanical Preparation.

Having transferred each explanted organ into an environment preferably free from environmental microbial contamination, the skilled personnel proceeds with the on table removal of the component of the organ destined for the production of the biomaterial. In-depth research has identified, in the component constituting the cornea, particularly in the connective layer of the stroma, the biological material with the most suitable characteristics for the production of a biomaterial suited to the subject purpose of the present invention.

The cornea, and preferably the connective component constituting the stroma, is explanted by incision of the limbus corneae with a special ophthalmic scalpel and blunt dissection of the stromal layer from the underlying layers using blunt scissors. Alternatively, for the removal of the stromal component, it is possible to use an injection of fluid (e.g. an injection of a sterile physiological solution, or, alternatively, a phosphate buffer saline solution at pH 7.4) between the different layers of the cornea, or another method currently used in ophthalmologic surgery.

The execution of the tissue removal procedure requires maximum care and technical stratagem necessary to obtain a uniform sample having dimensions suited to the production of the biomaterial. It is, therefore, possible to obtain tissue samples of generally roundish form (ovoidal in some animal species) having diameters of 4 or more centimetres (larger or smaller depending on the size of the animal), in any case, sufficient for the subsequent production of the biomaterial.

Repeated washings, preferably with a sterile physiological solution, or, alternatively, with a phosphate buffer saline solution at pH 7.4, of the biological tissue during the explantation help achieve a material which is free from impurities.

Particular care is also taken not to subject the material under discussion to pulling or distortion in order to preserve its biological and mechanical characteristics.

Upon termination of explantation, an additional washing of the tissue, preferably with sterile physiological solution, completes the preparation stage of the fresh tissue.

The explanted tissue is then preferably mounted on a support in order to keep its dimensional characteristics unchanged.

Then one proceeds with the housing of the tissue, preferably mounted on the support, in a special container containing the fixative suited to the subsequent treatment for the construction of the biomaterial.

Particular care is taken so that all the tissue surfaces come into equal contact with the fixative.

3. Chemical Treatment.

The tissue, preferably mounted on a suitable support, is then housed in special containers containing chemical solutions.

Fixing of the tissue preferably takes place with a solution of glutaraldehyde at variable concentrations from 0.1% to 5% (preferably 0.4%) in phosphate buffer saline solution at pH 7.4 for variable periods (preferably 3 months). However, shorter or more prolonged periods of tissue fixing can be used.

The aim of fixing the tissue by this procedure is to cause an increase in the cruciform bonds of the tissular collagen, a conclusive factor in giving the tissue greater resistance to biodegradation and in reducing or nullifying its antigenicity.

Alternative chemical solutions, at different pressures, are used in order to impart biological and mechanical characteristics which are particularly welcome in a biomaterial.

In the case of contact use, with the haematic flow of the biomaterial, subject of the invention, treatment is also envisaged of the same with the so-called bioactive materials (e.g. heparin, antibiotics, anticalcifying agents and drugs in general), in order to give additional potentially favourable characteristics (prevention of calcification phenomena, increased antithrombogenicity, etc.).

4. Construction of the End Product (Simple or Composite)

The biomaterial obtained from the previously described processing stages is subsequently taken from the containers, in which it had been subjected to the chemical fixing methods, in order to undergo additional processing procedures, preferably manual, by skilled personnel, to obtain products which may be used in the biomedical field, particularly in the field of reparative or replacement surgery of human or animal tissues or organs.

The biomaterial is subjected to macroscopic and microscopic inspection before being sent to the production line of the end products.

Possible anomalies in the previous processing stages are identified, so as to proceed with a selection of the materials fit for additional processing according to standardized parameters.

High magnification examination under polarized light allows the verification of the preservation of structural integrity of the collagen component of the fixed material, is the identification of damage or perforations of the biological tissue and the preservation of dimensional characteristics. Additional examinations can be carried out in order to guarantee the dispatch of biomaterial samples possessing the desired optimum characteristics to the final processing stage.

For the production of particular products (e.g. cardiac valvular prostheses) parameters are also assessed, namely the symmetry of flaps obtained from the biomaterial, the homogeneity of thickness, etc.

Biocompatible materials (for example, polyethyleneterephthalate, polytetrafluoroethylene) can be used, in conjunction with the biomaterial, for the production of composite prostheses.

Processing procedures, such as the dinking or modelling of the biomaterial, can be used for the production of biomaterial patches for various uses in the biomedical field, particularly in the reparative or replacement surgery of tissues or organs.

5. Sterilization and Packing

The simple or composite end products, obtained from the processing stages of the biomaterial, are then subjected to approval by standardized validation steps in order to exclude products which fail to conform to the characteristics and to the use, from the following stages.

The sterilization of the biomaterial preferably occurs by immersion in a solution of 0.6% glutaraldehyde and 20% ethanol in phosphate buffer saline solution at pH 7.4.

The sterilization of the biomaterial, like all the medical products destined for implantation in the human or animal organism, proves essential. The aim is to nullify the bacterial charge which might be present in the implants thus, in this way, preventing the onset of infections in the host organism.

Alternative sterilization methods of the biomaterial can include chemical agents (e.g. formaldehyde, etc.), gas (e.g. ethylene oxide), radiation (e.g. gamma or beta rays).

In addition, the cryoconservation of the biomaterial at extremely low temperatures can represent an additional method of conservation and sterilization.

Packing of the biomaterial takes place in specially made containers in order to keep the biological, mechanical and conservation characteristics in general of the biomaterial unchanged for prolonged time periods.

Washing of the biomaterial, by repeated passages in sterile physiological solution for standard times, is fundamental before implantation into the organism to remove any residue of chemical substances. This procedure is accepted practice in the course of all the implants of biological materials previously treated with chemical substances.

Applications

The biomaterial, subject of the present invention, has been used advantageously for the construction of cardiac valvular prostheses (the so-called "biological valves") with innovative characteristics not only due to the use of the biomaterial under discussion but due to the structural peculiarities and the structures expressly studied in order to improve the haemodynamic performance of the implants.

The valves produced have been the subject of in vitro and in vivo research for the examination of haemodynamic performance, duration and biological behaviour.

Construction of the valves made use of manual processing (dinking, folding, suture, etc.) of biomaterial segments according to the invention and a possible combination of the same with synthetic materials (e.g., polyethyleneterephthalate, polytetrafluoroethylene, etc.).

Prototypes of cardiac valvular prostheses have been made with a monocusp configuration, or with two, three and four flaps produced with the biomaterial main subject of the present invention.

The valves have been made of biological tissue using either just the biomaterial, subject of the invention, or a combination of the present biomaterial with other biomaterials, namely bovine or animal pericardium in general.

Cardiac valvular prostheses have been made by combining the biomaterial with synthetic tissues.

The biomaterial under discussion, in the shape of a patch or in tubular form has undergone in vitro and in vivo tests to verify its applicability in areas of the organism such as blood vessels, cavity organs, viscera, and as patches for the correction of congenital cardiac anomalies (interatrial or interventricular defects). Moreover, use of the biomaterial subject of the present invention is possible as a component of an artificial system of cardiocirculatory assistance, such as, for example, a membrane for an artificial heart, or a valve for an artificial heart.

BRIEF DESCRIPTION OF THE DRAWINGS

A non-limiting embodiment form of the present invention will now be described with reference to the enclosed designs, in which.

BEST MODE FOR CARRYING OUT THE INVENTION

Figure 1:
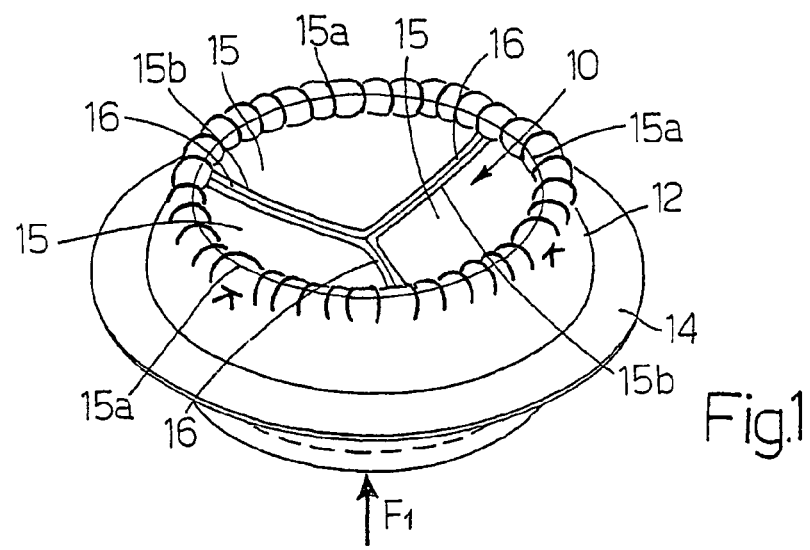
FIG. 1 shows an axonometric view of a cardiac valve including the biomaterial, main subject of the present invention.

In FIG. 1 a cardiac valve is denoted, as a whole, by 10.

This cardiac valve 10 includes a frame 11 (FIG. 2) of support that represents, as it were, the metal "soul" that supports the whole structure making up the cardiac valve 10 itself.

The metal frame 11 is advantageously, but not necessarily, made of polypropylene, or of an alloy based on titanium, aluminium and vanadium and is of basically toroidal shape.

On this toroidal frame 11 are affixed, in a way in itself known, an external cover part 12, for example made of Terylene or PTFE (polytetrafluoroethylene), and an internal cover part 13 made of a finely porous fluoroplastic material. The external part 12 also has a suture ring 14 (FIGS. 2, 3), which allows the fastening of the cardiac valve 10 by suture to the patient's heart. The fastening system of the external part 12 and of internal part 13 to the frame 11 is in itself known and will not be described in detail.

Figure 2:
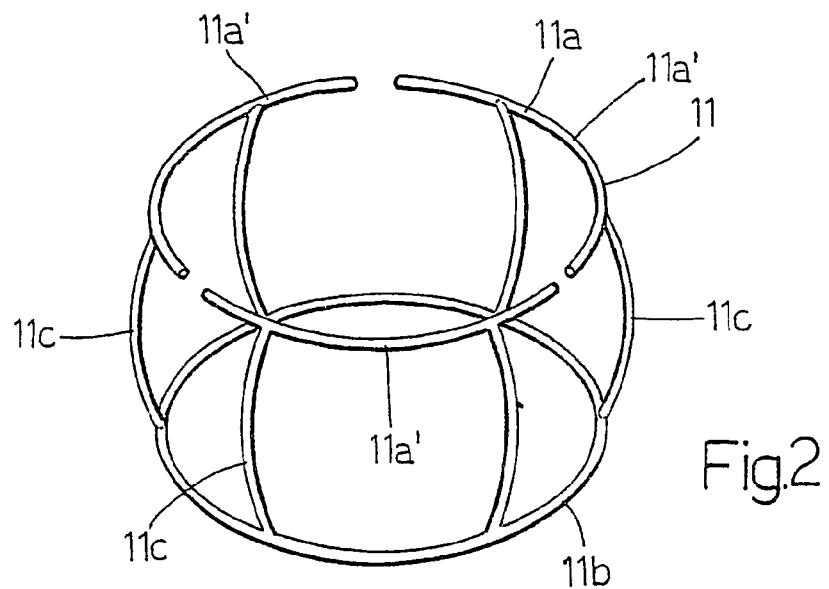
FIG. 2 shows an axonometric view of a support frame used in the cardiac valve of FIG. 1.
Figure 3:
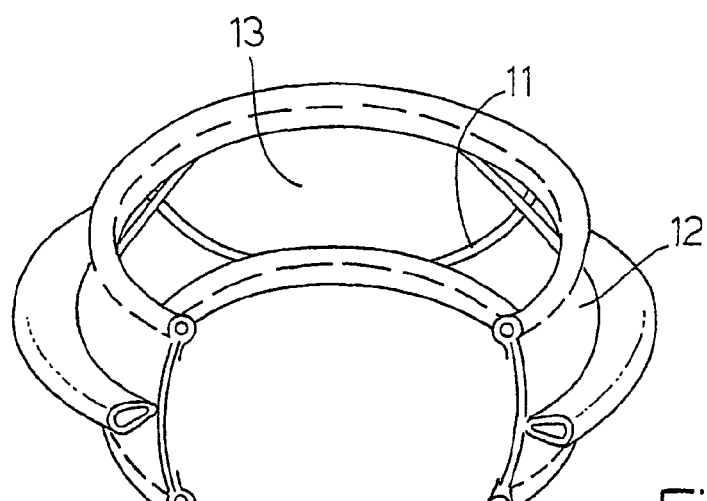
FIG. 3 represents an axonometric view of the cover of the frame of FIG. 2.

More particularly, with reference to FIG. 2, the frame 11 includes an upper moulding 11a, consisting, in turn, of a trio of arches 11a', a lower moulding 11b whose course is identical to that of the moulding 11a, and a series of slightly arched uprights 11c, each of which is integral with both the moulding 10a and moulding 11b. The slightly arched uprights 11c are responsible for the cited toroidal shape of the frame 11.

The particular toroidal shape of the cardiac valve 10 and the characteristics of the materials with which it is built are responsible for the elasticity of the same during the systole and diastole stage of the heart in which the valve 10 is implanted.

As shown in FIG. 1, the cardiac valve 10 is completed by a plurality of cusps 15, which in the embodiment form shown in the figure are three in number and shaped like a sector of a circle.

It is said incidentally that, even if there are three cusps 15 in the embodiment form shown, it is possible to consider alternatives presenting just one or two cusps.

The curved side 15a of each cusp 15 is sutured on the upper moulding 11a and on the attachment zone of the cover parts 12 and 13 at the upper moulding 11a itself, while each straight side 15b of the two straight sides 15b of each cusp 15 lightly rests on a straight side 15b of an adjacent cusp 15.

During the systole stage the blood is pushed in the direction F1 and, because of the energy it possesses manages, in passing through the valve 10, to deform the cusps 15 and to pass between the interstices 16 left free between two right sides 15b of two adjacent cusps 15.

Therefore, it is of extreme importance that the cusps 15 are made of a material having high mechanical characteristics, increased resistance to wear and to attack of chemical-biological origin.

As we have said in-depth research has identified, in the component constituting the cornea of fish, and especially in the connective layer of the stroma, the characteristics most suitable for the production of a biomaterial fit for the production of the cusps 15.

The invention claimed is:

1. A biomaterial consisting of stroma tissue from the cornea of a fish which has been isolated from other corneal tissue of the fish, said isolated stroma tissue having been treated such that the isolated stroma tissue has reduced antigenicity or greater resistence to biodegradation than the stroma tissue before treatment.

2. A method for effecting cardiocirculatory assistance in a patient comprising
(a) providing an artificial system with the biomaterial of claim 1; and
(b) implanting the system into the patient to effect the cardicirulatory assistance.

3. A prosthesis or implant comprising the biomaterial of claim 1 and support means for supporting the biomaterial in a blood vessel, cavity organ or viscus of a patient.

4. A method for repair of a blood vessel, cavity organ or viscus of an animal, the method comprising:
(a) providing the biomaterial of claim 1 in the form of a patch; and
(b) applying the patch to the blood vessel, cavity organ or viscus to effect a repair thereof.

5. The method as claimed in claim 4, wherein the patch is applied to correct a cardiac anomaly.

6. The biomaterial as claimed in claim 1, wherein the fish is a tuna.

7. A method for repair of a blood vessel, cavity organ or viscus of an animal, the method comprising:
   (a) providing the biomaterial of claim 6 in the form of a patch; and
   (b) applying the patch to the blood vessel, cavity organ or viscus to effect a repair thereof.

8. The method as claimed in claim 7, wherein the patch is applied to correct a cardiac anomaly.

9. A biomaterial comprising stroma tissue from the cornea of an animal which has been isolated from other corneal tissue of the animal, said isolated stroma tissue having been treated such that the isolated stroma tissue has reduced antigenicity or greater resistance to biodegradation than the stroma tissue before treatment, and further comprising a second material that is biocompatible with the isolated stroma tissue, wherein the second material is an artificial material selected from the group consisting of polyethyleneterephthalate and polytetrafluoroethylene.

10. The biomaterial as claimed in claim 9, wherein the animal is a fish.

11. The biomaterial as claimed in claim 10, wherein the fish is a tuna.

12. A biomaterial comprising stroma tissue from the cornea of an animal which has been isolated from other corneal tissue of the animal, said isolated stroma tissue having been treated such that the isolated stroma tissue has reduced antigenicity or greater resistance to biodegradation than the stroma tissue before treatment, and further comprising a second material that is biocompatible with the isolated stroma tissue, wherein the second material comprises a pericardium from an animal.

13. The biomaterial as claimed in claim 12, wherein the animal is a fish.

14. The biomaterial as claimed in claim 13, wherein the fish is a tuna.

15. In a cardiac valve comprising a support frame, means for covering the support frame, fastening means for fastening the cardiac valve to the heart of a patient, and at least one cusp that opens to blood flow during a systole stage of the patient's heart and closes the blood flow at a diastole stage of the patient's heart, the improvement wherein the cusp consists of stroma tissue from the cornea of an animal which has been isolated from other corneal tissue of the animal.

16. The cardiac valve of claim 15, where the stroma tissue is isolated from the cornea of a fish.

17. The cardiac valve of claim 16, wherein the fish is a tuna.

18. A prosthesis or implant comprising a biomaterial consisting of stroma tissue from the cornea of an animal which has been isolated from other corneal tissue of the animal, said isolated stroma tissue having been treated such that the isolated stroma tissue has reduced antigenicity or greater resistance to biodegradation than the stroma tissue before treatment, and support means for supporting the biomaterial in a blood vessel, cavity organ or viscus of a patient.

19. The prosthesis or implant as claimed in claim 18, wherein the animal is a fish.

20. The prosthesis or implant as claimed in claim 19, wherein the fish is a tuna.

* * * * *